United States Patent [19]

Jones et al.

[11] 4,171,699

[45] Oct. 23, 1979

[54] MERCAPTAN MODIFIED METHYL METHACRYLATE-ALPHA METHYL STYRENE COPOLYMER SYRINGE

[75] Inventors: William D. Jones, Jamesburg; Donald E. Hudgin, Princeton Junction, both of N.J.

[73] Assignee: Princeton Polymer Laboratories, Inc., Plainsboro, N.J.

[21] Appl. No.: 794,927

[22] Filed: May 9, 1977

[51] Int. Cl.$^2$ .............................................. A61M 5/00
[52] U.S. Cl. .................................... 128/218 S; 526/73
[58] Field of Search ................ 128/218 R, 218 S, 215, 128/219–220; 526/73, 329.2

[56] References Cited

U.S. PATENT DOCUMENTS

| | | | |
|---|---|---|---|
| 3,072,622 | 1/1963 | Ham | 526/73 |
| 3,135,723 | 6/1964 | Vandegaer | 526/329.2 X |
| 3,183,217 | 5/1965 | Sernink | 526/221 |
| 3,291,128 | 12/1966 | O'Neil | 128/218 R |

FOREIGN PATENT DOCUMENTS

| | | | |
|---|---|---|---|
| 806435 | 2/1969 | Canada | 128/218 R |
| 712861 | 8/1954 | United Kingdom | 128/218 R |
| 1123724 | 8/1968 | United Kingdom . | |

OTHER PUBLICATIONS

Walling et al., Copolymerization 70 J.A.C.S., 1543–1544, 4/1948.
Mitsui Petrochemical Ind. Ltd., TPX syringe advertisement.

*Primary Examiner*—Robert W. Michell
*Assistant Examiner*—C. F. Rosenbaum
*Attorney, Agent, or Firm*—Cushman, Darby & Cushman

[57] ABSTRACT

A steam sterilizable copolymer is prepared from 60 to 50% by weight of alpha methyl styrene and 40 to 50% by weight of methyl methacrylate. The copolymer is useful to make the barrel of syringe which is clear, water-white and shows no distortion upon steam sterilization for at least 20 minutes at 250° F.

19 Claims, 1 Drawing Figure

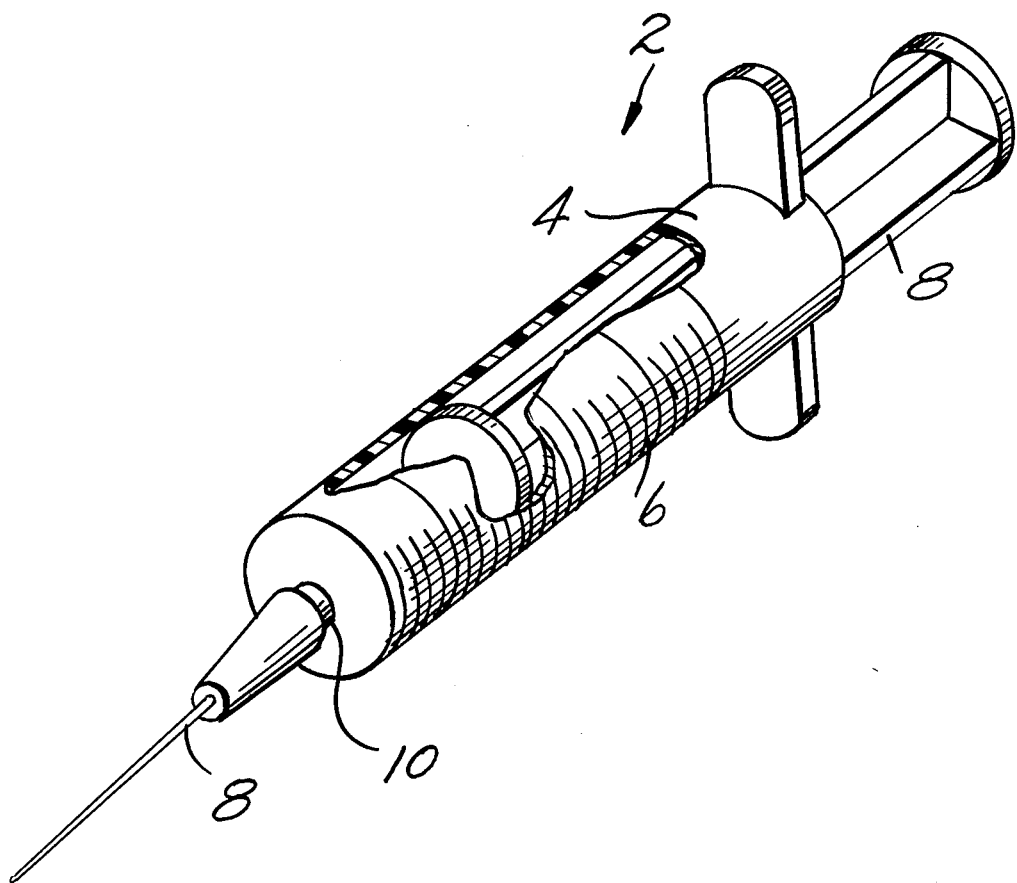

MERCAPTAN MODIFIED METHYL METHACRYLATE-ALPHA METHYL STYRENE COPOLYMER SYRINGE

BACKGROUND OF THE INVENTION

It is desirable to have a steam sterilizable, clear, water-white plastic syringe which is cheap enough to be expendible as a throw away after a single use. To date this has not been achieved. It is known to make syringes from 4-methylpentene-1 polymer (available commercially as TPX). However, this polymer is quite expensive, the selling price for the polymer alone recently being $1.67 a pound.

In the manufacture of syringes for the injection of pharmaceutical products glass has been the preferred product. This is based on factors such as clarity, modest price and steam sterilizability. In spite of many advantages glass has the disadvantage of relatively poor impact resistance and shattering when it is broken.

A number of plastics have been investigated as a potential replacement for glass in the manufacture of syringes to circumvent the problem of breakage. Polystyrene has acceptable clarity, color, and price, but it cannot be steam sterilized. Polycarbonate has acceptable clarity, color and can be steam sterilized but is high priced as is 4-methylpentene-1 polymer mentioned above. Polypropylene can be steam sterilized and is modestly priced but has poor clarity.

Walling et al., J. Amer. Chem. Soc. 70 (1948) 1543–1544 refer to copolymerization of alpha methyl styrene with methyl methacrylate. Reactivity ratios for the two monomers were determined. The polymerization was carried out at 60° C. in sealed tubes with benzoyl peroxide catalyst.

Ham U.S. Pat. No. 3,072,622 shows making copolymers of alpha methyl styrene and methyl methacrylate. While Ham claims reacting 10 to 40 parts by weight of alpha methyl styrene with 60 to 90 parts by weight of methyl methacrylate, in Examples I and II runs 11 and 12, he also discloses using 50 parts of alpha methyl styrene and 50 parts of methyl methacrylate. Ham on col. 2 lines 26–42 refers to Walling and points out that the Walling procedure gives low molecular weight polymers which are brittle and have low heat resistance which would have no utility as a plastic. Ham developed a process to overcome this and his copolymers are stated to be useful for making plastic articles by extruding, molding and casting. Sheets, rods, tubes, lenses and massive pieces can be made according to Ham. The products are stated to be useful in a manner similar to polymethyl methacrylate. The products of Ham are stated to be water white and to have high heat distortion temperatures, e.g., 140°–145° C. in Example II run 11 Table II.

Ham polymerizes in the absence of a solvent or water. While he only has a peroxide catalyst present in his examples he mentions that the polymerization can be improved by employing an organic disulfide or a mercaptan such as tertiary dodecyl mercaptan. Ham is assigned to the J. T. Baker Chemical Company.

Vandegaer U.S. Pat. No. 3,134,723 also assigned to J. T. Baker Chemical Company is directed to an improved process of copolymerizing 15 to 35 parts by weight of alpha methyl styrene with 65 to 85 parts by weight of methyl methacrylate. The improved technique is stated to reduce the time required for the reaction. The examples show various polymerization conditions including the use of tertiary dodecyl mercaptan as a polymerization regulator or stabilizer. Both peroxides and azo compounds are employed as catalysts. The reaction is carried out without the use of a solvent or water.

The copolymers are stated to have remarkable resistance to boiling water without losing their water-white optical clarity or shape or changing in physical dimensions. No mention is made, however, of resistance to steam sterilization at 250° F. (about 121° C.) The present inventors have tested commercial samples of alpha methyl styrene-methyl methacrylate copolymers made by the J. T. Baker Chemical Company as well as the copolymer of alpha methyl styrene and methyl methacrylate available commercially as Plexiglass II and found that after injection molding followed by steam sterilization at 250° F. they were distorted and became opaque. In some instances shrinkage was as much as 30%.

SUMMARY OF THE INVENTION

It has now been found that there can be prepared copolymers by reacting 40 to 50% by weight of methyl methacrylate with 60 to 50% by weight of alpha methyl styrene in the presence of an alkyl mercaptan as a chain transfer agent. The resultant copolymer is clear, water-white and molded articles, e.g., prepared by injection molding or compression molding have practically zero shrinkage (i.e., they are dimensionally stable) when subjected to steam sterilization at 250° F. for 20 minutes or longer. Furthermore, the clarity and water-white appearance are retained after such steam sterilization.

Preferably the molded objects are prepared by injection molding.

The copolymers of the invention are particularly suitable for making syringes, e.g., by injection molding, which must be subjected to steam sterilization at 250° F. for 20 minutes. While it is preferable to make both the barrel and plunger of the syringe from the novel copolymer, it is of primary importance that the barrel be made of it. The plunger can be made of any other plastic which can be molded and will withstand steam sterilization for at least 20 minutes without change in its dimensions. Thus, there can be used for example thermosetting resins such as melamine-formaldehyde, urea-formaldehyde and thermosetting polyesters or thermoplastic resins such as polypropylene for example. It is not essential that the plunger be transparent which is why such other materials can be employed as the plunger. However, the plunger is preferably at least translucent and more preferably is transparent. Most preferably it is the novel alpha methyl styrene-methyl methacrylate copolymer of the invention. The barrel of the invention can either be unmarked or marked in conventional manner to indicate the volume when the syringe is completely or partly full of liquid. The invention is especially suitable in making disposable (i.e., throw away) syringes, but it is also useful with reusable syringes.

The plunger and barrel are normally sterilized at the same time. The plunger can be sterilized either when it is inside the barrel or when it is separate from the barrel.

As the alkyl mercaptan there is normally used a higher alkyl mercaptan, e.g., of 6 to 20 carbon atoms such as hexyl mercaptan, t-dodecyl mercaptan, octyl mercaptan, lauryl mercaptan, cetyl mercaptan, octadecyl mercaptan or eicosanyl mercaptan. The mercaptan acts as a chain transfer agent and it is believed that the polymer has a relatively narrow molecular weight distribution. The amount of mercaptan employed is quite small, generally less than 1% of the total weight of the monomers, e.g., as little as 0.01% of the monomers. Preferably it is about 0.2%.

The conventional free radical catalysts can be used, e.g., peroxides, hydroperoxides and azo compounds, the azo compounds being preferred. Thus, there can be used 2,2'-azobis(2-methyl-propionitrile), azo-di(cyclohexane carbonitrile), benzoyl peroxide, cumene hydroperoxide, potassium persulfate, hydrogen peroxide, dicumyl peroxide, t-butyl hydroperoxide, di-t-butyl peroxide, etc. The catalysts are used in conventional amounts, e.g., 0.01 to 0.8% by weight of the monomers. Preferably the catalyst is about 0.35% of the monomers.

The polymerization reaction is preferably carried out in water in the presence of an emulsifying agent. There can be used any of the conventional emulsifying agents, e.g., anionic, cationic, amphoteric and non-ionic emulsifiers. Examples of such emulsifiers include potassium oleate, potassium stearate, sodium decyl sulfonate, sodium dodecyl sulfonate, sodium decyl sulfate, sodium dodecyl benzene sulfonate, sodium dioctyl sulfosuccinate, sodium nonylbenzenetetraoxy-ethylene sulfate, p-nonylphenyl-ethylene oxide adduct having 4, 6, 15, 20 or 30 ethylene oxide units, p-isooctyl phenol-ethylene oxide adduct having 9.5 ethylene oxide units, lauryl poly(ethyleneoxy) ethanol having 4 or 23 ethylene oxide units, cetyl pyridinum chloride. A full discussion of emulsifiers is found in the Encyclopedia of Polymer Science 5, 801–857.

The preferred emulsifiers are complex organic phosphate esters which are mixtures of monoesters of the formulae

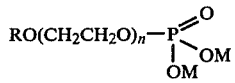

and diesters of the formula

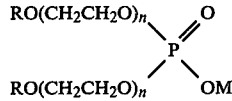

where R is alkyl or alkylaryl, n is the average number of ethylene oxide units, e.g., 3 to 20. Thus, there can be used isooctyl alcohol ethoxylated and phosphated, dodecyl alcohol ethoxylated and phosphated, nonylphenol ethoxylated and phosphated, dinonyl phenol ethoxylated and phosphated. The preferred emulsifier is GAFAC RE-610 which is a higher alkyl phenol which has been ethoxylated and phosphated. It has a specific gravity of 1.10–1.12 at 25° C., an acid number to the 1st inflection point (pH 5–5.5) of 62–72, an acid number to the 2nd inflection point (pH 9–9.5) of 110–125, a pH of a 10% solution of <2.5, a pour point, ASTM of <1° C. It is in the free acid rather than salt form.

BRIEF DESCRIPTION OF THE DRAWINGS

The single FIGURE of the drawings is a perspective view partially broken away of an injection molded syringe according to the invention.

Referring more specifically to the drawings there is shown a syringe indicated generically at 2. The syringe comprises a barrel 4 made of an injection molded alpha methyl styrene-methyl methacrylate copolymer (1:1 mole ratio). The barrel is graduated as shown by the markings 6 thereon. Fitting into the barrel is the plunger 8 which is made of the same injection molded copolymer as the plunger. (As stated above, the plunger can be made of any plastic which is dimensionally stable at 250° F. for 20 minutes.) Opposite to the end of the barrel which receives the plunger there is provided a needle 8 which can be attached to the barrel in any conventional manner, e.g., the end of the barrel 10 can be threaded to receive a needle which is matingly threaded to the threads on the barrel.

DESCRIPTION OF THE PREFERRED EMBODIMENT

Unless otherwise indicated all parts and percentages are by weight.

EXAMPLE 1 (COMPARATIVE EXAMPLE)

One hundred and eight grams of alpha methyl styrene and ninety-two grams of methyl methacrylate (1:1 mole ratio) were copolymerized in 600 grams of distilled water containing 8 grams of GAFAC RE-610 (manufactured by GAF Corporation) and adjusted to a pH of 6.8 with sodium hydroxide. The polymerization, conducted under nitrogen at 80° C. with agitation was initiated by 0.7 gram 2,2'-azobis(2-methyl-propionitrile). After 18 hours at 80° C. the conversion from monomer to polymer was about 60%. The latex was frozen, thawed, filtered, washed three times with isopropanol at 50° C. and dried in an air circulating oven at 60° C.

The dried polymer had a Brabender Plasticorder® reading of 1700 and was essentially water clear and colorless. An injection molded sample subjected to 250° F. in a steam sterilizer for 20 minutes showed about 30% shrinkage.

EXAMPLE 2 (ACCORDING TO THE INVENTION)

Example 1 was repeated except that 0.4 gram of lauryl mercaptan was added to the monomers. Polymerization was continued for 18 hours at 80° C. and resulted in about 62% conversion.

The latex was frozen, thawed, filtered, washed three times with isopropanol at 50° C. and dried in an air circulating oven at 60° C.

The dried polymer had a Brabender Plasticorder® reading of 1400 and was essentially water clear and colorless. An injection molded sample sterilized at 250° F. for 20 minutes in a steam autoclave showed no shrinkage.

The syringes of the present invention can be used wherever sterile syringes are normally used.

What is claimed is:

1. A clear, water-white molded syringe barrel capable of being sterilized at 250° F. for 20 minutes without shrinkage while retaining its clear, water-white appearance, said syringe being made of a copolymer of 50 to 60% by weight of alpha methyl styrene and 50 to 40% by weight of methyl methacrylate.

2. A syringe barrel according to claim 1 made from 54 parts by weight alpha methyl styrene and 46 parts by weight of methyl methacrylate.

3. A syringe barrel according to claim 2 which is an injection molded barrel.

4. A syringe barrel according to claim 3 which is sterile as a result of having been subjected to sterilization at a temperature of at least 250° F. for at least 20 minutes and is characterized by being water-white, clear and free of shrinkage after such sterilization.

5. A syringe barrel according to claim 2 which is sterile as a result of having been subjected to sterilization at a temperature of at least 250° F. for at least 20 minutes and is characterized by being clear, water-white and free of shrinkage after sterilization.

6. A syringe barrel according to claim 1 which is an injection molded barrel.

7. A syringe barrel according to claim 6 which is sterile as a result of having been subjected to sterilization at a temperature of at least 250° F. for at least 20 minutes and is characterized by being clear, water-white and free of shrinkage after sterilization.

8. A syringe barrel according to claim 1 which is sterile as a result of having been subjected to sterilization at a temperature of at least 250° F. for at least 20 minutes and is characterized by being clear, water-white and free of shrinkage after sterilization.

9. A syringe comprising a combination of the barrel of claim 1 and a plunger of a plastic and is characterized by being dimensionally stable when subjected to steam sterilization at 250° F. for 20 minutes.

10. A syringe according to claim 9 wherein the plunger is made of polypropylene.

11. A syringe according to claim 9 wherein the plunger is made of a plastic which is clear, water-white and dimensionally stable when subjected to steam sterilization at 250° F. for 20 minutes.

12. A syringe according to claim 11 wherein the plunger is made of the same copolymer as the barrel.

13. A syringe according to claim 9 wherein the barrel is injection molded.

14. A syringe according to claim 13 wherein both the barrel and plunger are injection molded.

15. A syringe according to claim 13 wherein the barrel is made from 54 parts by weight of alpha methyl styrene and 46 parts by weight of methyl methacrylate.

16. A syringe comprising in combination a needle and the barrel and plunger of claim 15.

17. A syringe according to claim 16 which is sterile as a result of having been subjected to steam sterilization at 250° F. for 20 minutes.

18. A syringe comprising in combination a needle and the barrel and plunger of claim 13.

19. A syringe according to claim 18 which is sterile as a result of having been sterilized by being subjected to steam sterilization at 250° F. for 20 minutes.

* * * * *